(12) United States Patent
Yu et al.

(10) Patent No.: US 11,262,327 B2
(45) Date of Patent: Mar. 1, 2022

(54) METHODS OF FABRICATING A BIOCHIP FOR DETECTING OR SEQUENCING BIOMOLECULES

(71) Applicant: Hai Kang Life Corporation Limited, Shatin (HK)

(72) Inventors: Cheung Hoi Yu, Shatin (HK); Bo Liang Jia, Shatin (HK); Cheng Chang Lai, Shatin (HK)

(73) Assignee: Hai Kang Life Corporation Limited, Hong Kong (HK)

(*) Notice: Subject to any disclaimer, the term of this patent is extended or adjusted under 35 U.S.C. 154(b) by 372 days.

(21) Appl. No.: 16/446,754

(22) Filed: Jun. 20, 2019

(65) Prior Publication Data

US 2019/0302094 A1 Oct. 3, 2019

Related U.S. Application Data

(62) Division of application No. 14/948,835, filed on Nov. 23, 2015, now Pat. No. 10,379,101.

(51) Int. Cl.
*G01N 27/327* (2006.01)
*B01L 3/00* (2006.01)
(Continued)

(52) U.S. Cl.
CPC .......... *G01N 27/3276* (2013.01); *B01L 3/502* (2013.01); *B03C 5/005* (2013.01);
(Continued)

(58) Field of Classification Search
None
See application file for complete search history.

(56) References Cited

U.S. PATENT DOCUMENTS 5,187,096 A  2/1993  Giaever et al.
8,592,153 B1  11/2013  Bustillo et al.
(Continued)

FOREIGN PATENT DOCUMENTS

EP  2554683 A1  2/2013
EP  2677307 A1  12/2013
WO  2013109877 A2  7/2013

OTHER PUBLICATIONS

European Search Report Application No. EP 16 15 3373 Completed: Mar. 22, 2017; dated Mar. 31, 2017 15 pages.

*Primary Examiner* — J. Christopher Ball
(74) *Attorney, Agent, or Firm* — Ware, Fressola, Maguire & Barber LLP

(57) ABSTRACT

Methods for fabricating a biochip for detecting or sequencing biomolecules are shown. Such a biochip may for instance include: a base member; a dielectric layer deposited on the base member and having at least two rows of discrete recesses formed thereon; and two or more electrodes sandwiched between the base member and the dielectric layer and running under respective row of discrete recesses, the two or more electrodes separated from each other along lengths thereof by a portion of the dielectric layer; wherein the dielectric layer defines a continuous operation surface above the electrodes and on which the discrete recesses are deposited for detecting or sequencing of biomolecules, when an electric field is applied through the electrodes, a field gradient is created to draw a biomolecule towards a preferred part of the operation surface.

8 Claims, 16 Drawing Sheets

(51) Int. Cl.
*B03C 5/02* (2006.01)
*B03C 5/00* (2006.01)
*C12Q 1/6869* (2018.01)
*G01N 27/447* (2006.01)
*G01N 33/487* (2006.01)

(52) U.S. Cl.
CPC ............ *B03C 5/026* (2013.01); *C12Q 1/6869* (2013.01); *G01N 27/44756* (2013.01); *G01N 33/48721* (2013.01); *B01L 3/502707* (2013.01); *B01L 2300/0636* (2013.01); *B01L 2300/16* (2013.01); *B01L 2400/0415* (2013.01); *B03C 2201/26* (2013.01); *G01N 27/44791* (2013.01)

(56) References Cited

U.S. PATENT DOCUMENTS

| | | |
|---|---|---|
| 2003/0146100 A1 | 8/2003 | Huang et al. |
| 2005/0084865 A1* | 4/2005 | Yu .................... C12Q 1/6834 435/6.11 |
| 2013/0273640 A1 | 10/2013 | Krishnan et al. |
| 2014/0291152 A1 | 10/2014 | Conoci et al. |
| 2015/0084099 A1 | 3/2015 | Shen et al. |

* cited by examiner

METHODS OF FABRICATING A BIOCHIP FOR DETECTING OR SEQUENCING BIOMOLECULES

BACKGROUND OF THE INVENTION

The present invention relates to a biochip for the determination of the concentration of one or more types of specific biomolecules in a sample and its fabrication, for example particularly, but not exclusively, a biochip and its fabrication.

Nowadays, fast and high throughput biomolecular based detection devices tend to be miniaturized and high-level of integration. A general term for such devices is called "biochip". A biochip composes of a substrate for identifying the target from the sample solution being dispensed onto the substrate. Various sensing parts or the biomolecular reactants are facilitated on the substrate depending on specific applications. To enhance the in situ biochemical reaction efficiency, a close distance and locally high concentration of the reactant are both necessary. Therefore, efforts have been made to actively transport and replenish the target molecules, because these movements will increase opportunities for the target entities to meet/react with their counterparts, i.e. probe entities/biomolecules, which are normally immobilized on the substrate. Electrokinetics (EK) technologies have been developed and widely used as a mechanical-part-free, flexible and highly programmable tool for fluid and microparticle manipulation, especially in Lab-On-A-Chip (LOAC) platforms. Currently, there are some limitations in EK manipulation in LOAC devices. Under DC electric field regime, electrophoresis (EP) technology has been widely applied, such as the well-known gel electrophoresis. In general, DC electric field is only effective for either positively or negatively charged entities at a time. For biomolecules having complex conformations and charge conditions, it is difficult to manipulate EP transportation with good consistency and efficiency. Besides, even the highly corrosion-resistant electrode, like Platinum (Pt), will degrade with the operation time, which would also affect the accuracy and efficiency of such devices. When using AC electric field, dielectrophoresis (DEP) have become an outstanding technology in manipulating any charged and neutral microparticles. The major drawback of DEP is the short effective range, while other AC electrohydrodynamic (EHD) effects have been proven capable of driving fluids in longer range. However, the fluid flow is not efficient for confining and concentrating small molecules like nucleic acids.

Therefore, we seek to provide a comprehensive and robust solution to increase the efficiency of biochemical reaction through the conceptual design of device structures and fabrication method for combinational EK manipulations.

SUMMARY OF THE INVENTION

According to the invention, there is provided a biochip for detecting or sequencing biomolecules comprising:
  a base member;
  a dielectric layer being deposited on the base member and having at least two rows of discrete recesses being formed thereon; and
  two or more electrodes being sandwiched between the base member and the dielectric layer and running under respective row of discrete recesses, the two or more electrodes are separated from each other along length by a portion of the dielectric layer;
  wherein the dielectric layer defines a continuous operation surface above the electrodes and on which the discrete recesses are formed for detecting or sequencing of biomolecules, when an electric field is applied through the electrodes, a field gradient is created to draw biomolecules towards a preferred part of the operation surface.

Preferably, the recesses comprise one or more well and furrow formed between two rows of wells.

More preferably the furrow separates the two or more electrodes.

Advantageously, each electrode extends across the base member and is common to the wells in a same row.

More advantageously, the electrode comprises an elongate stripe of electric conducting material.

Preferably, the electrode is deposited underneath the dielectric layer.

Preferably, the electrode has a predetermined width of about 10 nm to 1 mm.

More preferably, the electrode has a predetermined thickness of about 1 nm to 1 mm.

Yet more preferably, the dielectric layer has a thickness of about 1 nm to 1 mm.

It is preferable that each well has a predetermined width of about 10 nm to 1 mm and has to be smaller than the predetermined width of the electrode as described above.

It is advantageous that each well has a predetermined depth of about 1 nm to 1 mm and has to be smaller than the thickness of the dielectric layer as described above.

Preferably the furrow has a predetermined width larger than twice the thickness of the dielectric layer as described above and smaller or equal to the width of the electrode as described above.

Preferably, the dielectric layer comprises a dielectric material selected from a group consisting of silicon oxide, silicon nitride, aluminum oxide and titanium oxide.

More preferably, the base member comprises a layer of thermal oxide deposited on a layer of silicon substrate.

Yet more preferably, one or more probe entities are attached to the operation surface in the recesses for catering the use of a low frequency electric field to create a field gradient that draws target entities towards the recess.

It is preferable that one or more probe entities are attached to the operation surface and outside of the recesses for catering the use of a high frequency electric field to create a field gradient that forces target entities towards operation surface outside the recess.

In another aspect of the invention there is provided a method of fabricating the biochip as described above comprising the steps of:
  a) providing a base member;
  b) photomasking an upper surface on the base member;
  c) etching two or more recesses on the upper surface;
  d) depositing a dielectric material on an upper layer over the two or more recesses;
  wherein the two or more recesses define a contour on the upper surface, the dielectric material adopts the contour and hardens to form a contoured operation surface.

Preferably, the base member comprises a metal layer deposited on a thermal oxide layer, the metal layer defines the upper surface on which a first round of the steps b) and c) are conducted to form the two or more recesses.

More preferably, a second round of steps b) and c) are conducted on the upper surface and between the two recesses to create a further recess therebetween which defines the upper layer on which step d) is performed.

Yet more preferably, the step d) is conducted after the first round of steps b) and c) to form a further upper surface, thereafter a second round of steps b) and c) are conducted on the further upper surface to further define the contour and form the upper layer.

Advantageously, the second round of steps b) and c) create one or more further recesses between the two or more recesses formed by the first round of steps b) and c).

More advantageously, the base member includes at least a thermal oxide layer which defines the upper surface and a first round of steps b) and c) are conducted on the upper surface to define the contour.

It is advantageous that the method further comprising the step of depositing a layer of metal onto the upper surface to form a further upper surface which adopts the contour.

Preferably, wherein a second round of steps b) and c) is conducted on the further upper surface to create one or more further recesses between the two recesses to further define the contour and form the upper layer.

More preferably, a step d) is conducted on the upper layer such that the dielectric material adopts the further defined contour and hardens to form a contoured operation surface.

In a further aspect of the invention there is provided a method of fabricating the biochip comprising the steps of:
a) providing a base member which includes a metal layer deposited on a thermal oxide layer;
b) photomasking an upper surface on the metal layer;
c) etching two or more recesses on the upper surface;
d) depositing a dielectric material on the upper surface forming an upper layer over the two or more recesses;
e) photomasking the upper layer;
f) etching a recess on the upper layer;
g) depositing a dielectric material on the upper layer over the recesses;
wherein the recesses define a contour on the upper surface and the upper layer, the dielectric material adopts the contour and hardens to form a contoured operation surface.

In an even further aspect of the invention there is provided a method of fabricating the biochip comprising the steps of:
a) providing a base member which includes a metal layer deposited on a thermal oxide layer, the metal layer defines the upper surface on which a first round of steps b) and c) are conducted to form the two or more recesses;
b) photomasking an upper surface on the base member;
c) etching two or more recesses on the upper surface;
d) conducting a second round of steps b) and c) on the upper surface and between the two recesses to create a further recess therebetween which defines an upper layer;
e) depositing a dielectric material on an upper layer over the recesses;
wherein the recesses define a contour on the upper layer, the dielectric material adopts the contour and hardens to form a contoured operation surface.

In another aspect of the invention there is provided a method of fabricating the biochip comprising the steps of:
a) providing a base member which includes at least a thermal oxide layer which defines the upper surface and a first round of steps b) and c) are conducted on the upper surface;
b) photomasking an upper surface on the base member;
c) etching a recess on the upper surface;
d) depositing a layer of metal onto the upper surface to form a further upper surface which adopts the contour of the upper surface;

e) a second round of steps b) and c) is conducted on the further upper surface to create further recess on either side of the first formed recess to further define the contour and form the upper layer
d) depositing a dielectric material on an upper layer over the recesses;
wherein the dielectric material adopts the contour on the upper layer and hardens to form a contoured operation surface.

BRIEF DESCRIPTION OF DRAWINGS

The invention will now be more particularly described, by way of example only, with reference to the accompanying drawings, in which:

FIG. 4A shows the circular recess without EK operation, FIG. 4B shows the EK operation of the circular recess under a low frequency AC electric field which is applied across electrodes of the biochip, indications are provided to show direction of the long range fluid transport and the short range fluid transport or localized regulation, FIG. 4C shows the EK operation under a medium frequency of AC electric field applied across the electrodes of the biochip, indications are provided showing the direction of the long range fluid transport and the short range fluid transport or localized regulation, FIG. 4D shows the EK operation under a high frequency of AC electric field applied across the electrodes of the biochip, indications are provided to show the direction of the long range fluid transport and the short range fluid transport or localized regulation;

DETAILED DESCRIPTION OF EMBODIMENTS

Figure 1A:
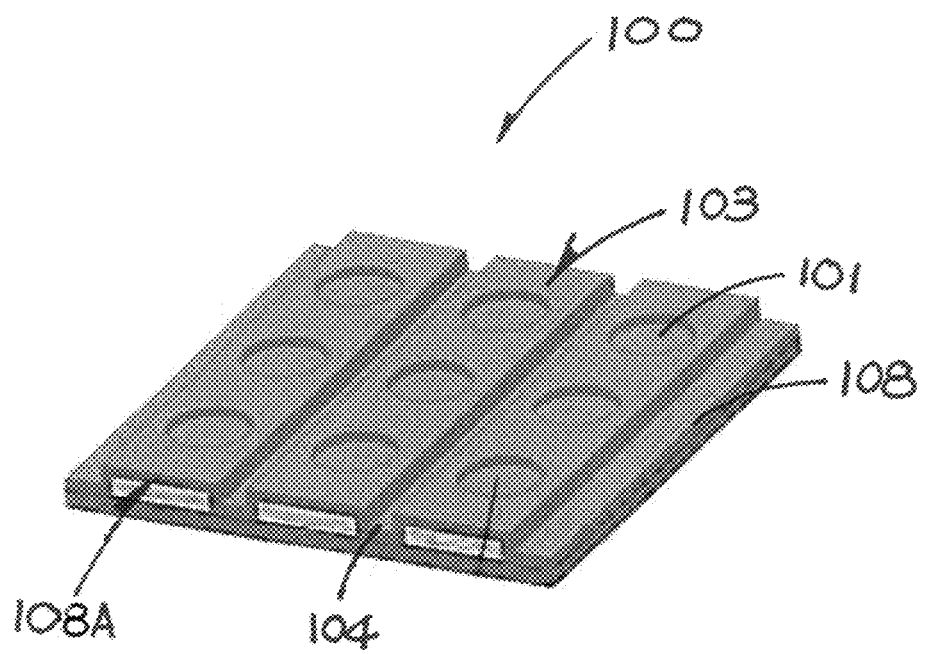
FIG. 1A is a perspective view of the biochip in accordance with the invention.
Figure 1B:
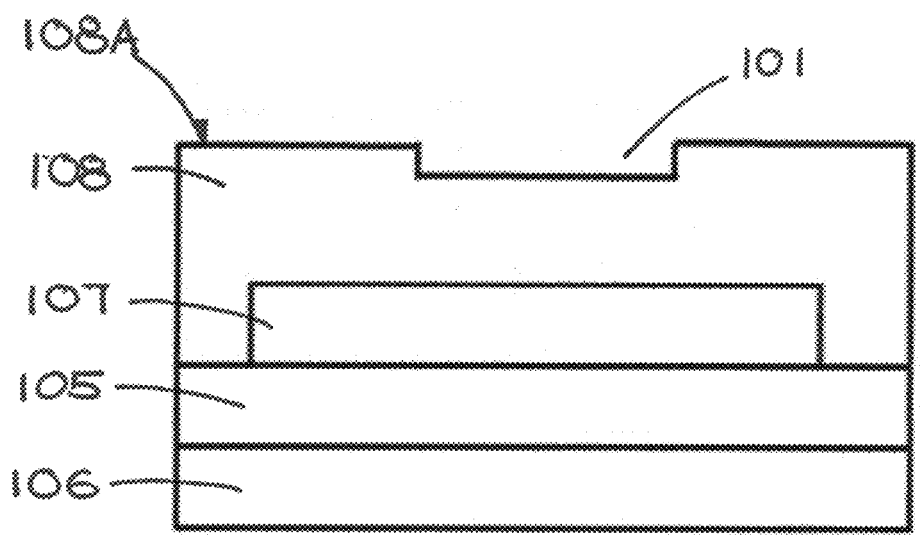
FIG. 1B is a schematic cross-sectional representation of the biochip in FIG. 1A.

Referring to FIGS. 1A and 1B of the drawings, there is shown an embodiment of a biochip 100 in accordance with the invention. Two or more discrete wells/recesses 101 are formed on an operation surface 108A. These wells/recesses are aligned to form a plurality of rows of wells/recesses 103. These rows 103 run parallel to one another and extend across the biochip 100. Each row 103 is separated by a recess in the form an elongated furrow 104. The shape of the wells/recesses 103 can be of any size and shape.

The term recess may be used to describe any indentation including wells 103 and furrow 104.

As shown in FIG. 1B, the biochip 100 is a lamination of or an array of layers of material. It has a base member which may include a layer of thermal oxide 105 deposited on a layer of silicon substrate 106. Stripes of conducting material 107 is placed on the layer of thermal oxide 105 forming the electrodes 107 of the biochip 100 that runs underneath each row 103. A layer of dielectric material 108 is deposited on the electrodes 107 to form an operation surface 108A of the biochip. The electrodes 107 are separated from one another by the furrow 104.

The discrete wells/recesses 101 and the furrow 104 are formed on the operation surface 108A in the form of a concave structure and a groove respectively. In other words, the operation surface is a contoured operation surface 108A. Probe entities 109 are attached to the operation surface 108A in conventional manner.

Figures 16, 17:
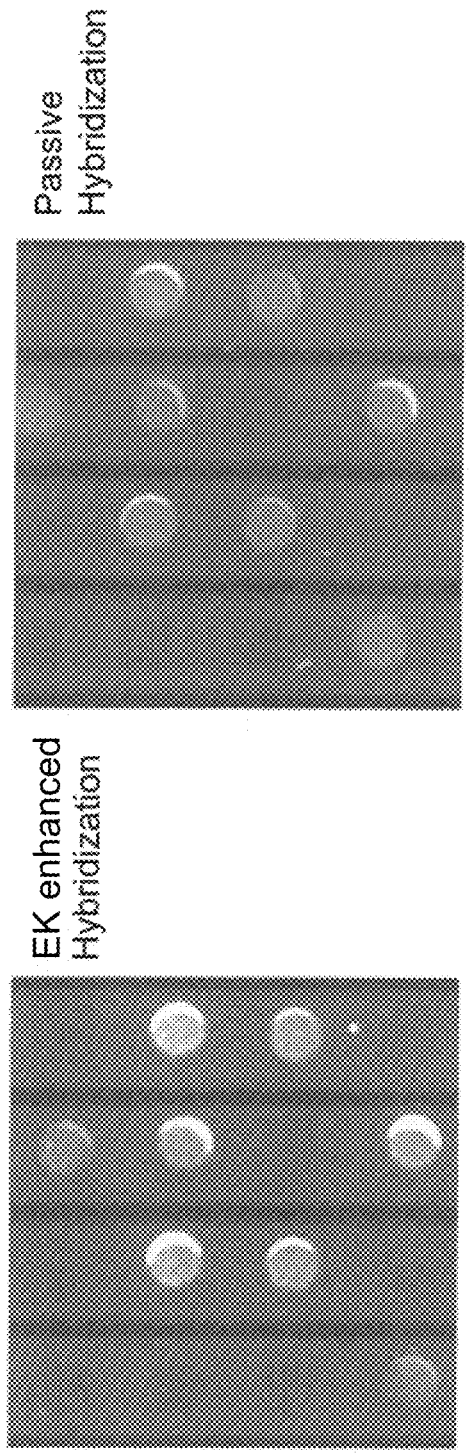
FIG. 16 is a photographical illustration of a part of the biochip in FIG. 1 demonstrating a comparison between the concentration of bound target to probe biomolecules under passive diffusion and the concentration of bound target to probe biomolecules under electrokinetically enhanced transportation for a same period of time.
FIG. 17 showing the pattern of immobilized probe biomolecules and the meaning of the probe biomolecules in the region of the experimented biochips shown in FIG. 16.
Figure 18:
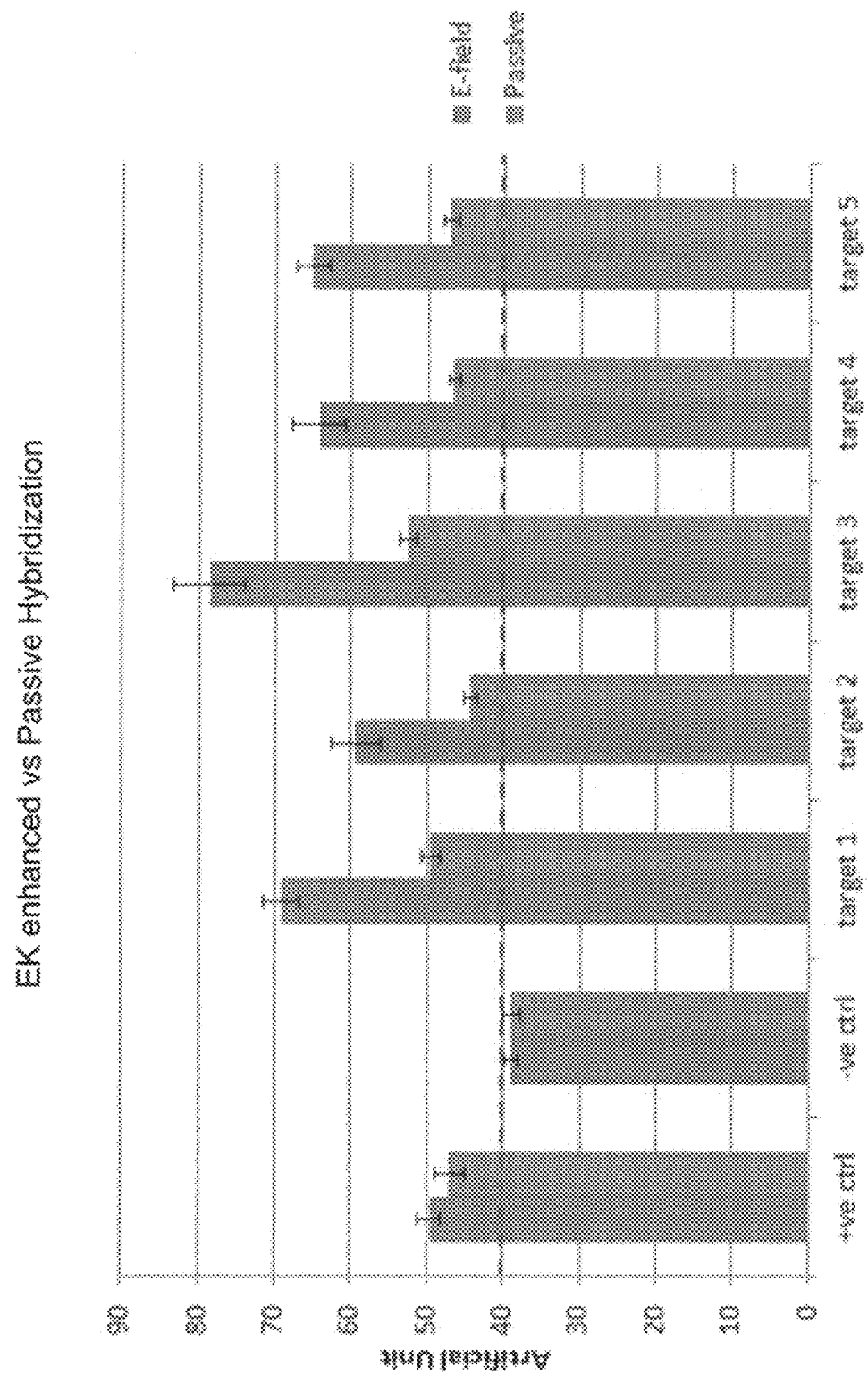
FIG. 18 is a bar chart comparing binding efficiencies represented in artificial unit intensity of electrokinetically enhanced transportation and binding efficiencies represented in artificial unit intensity of passive diffusion.

The biochip 100 when in use is covered by an aqueous solution with target entities disbursed therein which forms the medium for EK operation. The electrode arrays 107 is embedded under insulating layers such as the layer of dielectric material 108. This insulating layer prevents electrode from direct contact with the medium solution, leading electrochemical reaction, namely, electrolysis. By applying time varying electric field, the electric field is able to penetrate into the solution medium above the insulating surface. The existence of electric field strength in the medium can induces electrokinetic fluid flow and particle movement. On the surface of insulating layer 108, wells/recesses structures are provided to specifically regulate EK effects and concentrate target entities to the reaction sites where the probe entities are immobilized. With the increased local concentration, the opportunity of collision between target entities with the corresponding probe entities is enhanced. This process is achieved by DEP forces and ACEO/ACET fluid flow on the chip surface, and is far more efficient than passive diffusion in conventional reaction devices. An example is shown in FIGS. 16 and 18 and will be described later.

The biochip 100 is capable of manipulating fluid flow and assists surface focusing efficiency. The electrokinetic forces acting on target entities, such as EP and DEP, strongly rely on the field strength and the gradient of field strength square, respectively. However, the electric field strength attenuates exponentially into the medium, which confines the effective range of direct EK force on particles within a very short distance above electrode 107 surface. In this case, electrode array 107 is in planar manner, which is designated to induce long range fluid flows by ACEO and/or ACET effects under AC electric field. The ACEK induced fluid flows are patterned in a circulating manner, which can continuously refresh target entities in surface fluid with those in the bulk fluid.

Finally, by applying AC electric field to the biochip 100, target entities suspended in an aqueous solution are driven to the reaction sites on the chip surface via induced fluid flows. The surface structures further regulate the flow and concentrate the target entities to designated reaction sites with the assistance of DEP forces. The fluid flow circulation, in the meantime, acts to replenish the target entities from the bulk solution. Thus, with the combination of EK effects, both long range and short range manipulation are achieved. The resulting reaction efficiency can be enhanced from diffusion-based mechanism.

Figure 19:
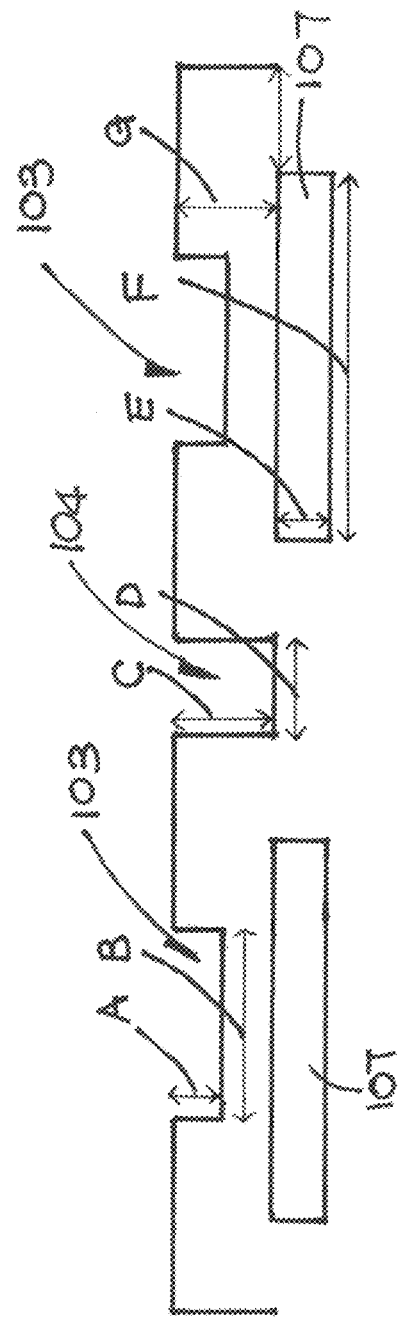
FIG. 19 is a schematic representation showing various dimension of the biochip.

In more detail, as shown in FIG. 19, width (B) of the discrete well/recess 101 is about 10 nm to 1 mm and would be smaller than the width (F) of the electrode 107 which is about 10 nm to 1 mm. Depth (A) of the well/recess 101 is about 1 nm to 1 mm and is smaller than thickness (G) of the dielectric layer 108 which is about 1 nm to 1 mm. The width (D) of the furrow 104 is larger than twice the thickness (G) of the dielectric layer 108 and smaller or equal to the width (F) of the electrode 107. The depth (C) of furrow 104 is equal to the thickness (E) of the electrode 107 which is about 1 nm to 1 mm. The discreet wells/recesses 101 have sharp upper rims with edge radius that is equal to the excess length of the thickness (G) of the dielectric layer 108 over the depth (A) of the well/recess 101. The discreet furrows 104 also have sharp upper rims with an edge radius which is equal to the thickness (G) of the dielectric layer 108. In summary, the smaller the edge radius, the greater an electric gradient is established in the medium adjacent the rim and edge when electric field is applied to the electrode.

CMOS fabrication techniques and processes for wafer-level production are used to create the biochip 100. There are four crucial layers. The biochip substrate is silicon wafer 106. Thermal oxidation is performed to create a foundation layer, a thermal oxide layer 105 for metal deposition. Sputtering method is used to form a metal layer 107 and pattern it into arrays of microelectrodes by photolithography. Then a dielectric layer 108 is deposited on the metal layer 107 for protecting the electrodes 107 and insulation. The wells/recesses 101 and furrows 104 are formed by photomasking and etching by photolithography. The materials of the dielectric layer will be detailed below.

The silicon substrate 106 is preferably a substrate of silicon based materials and solid polymers materials. The layer of dielectric material 108 is preferably an insulating layer made of silicon oxide, silicon nitride, titanium oxide or other dielectric materials.

Now we introduce the mechanism and controlling conditions of EK manipulation on the biochip.

The array of electrodes 107, more preferably microelectrodes, are embedded in the silicon substrate 106 preferably a silicon chip to create non-uniform distribution of electric field in the solution medium. Multiple EK effects due to non-uniform electric field are responsible for concentrating target entities, inducing fluid flow/enabling circulation above the biochip 100. Micro- or submicro-scaled target entities, such as biomolecules for example nucleic acid, suspended in the solution medium are being transported and circulated close to the operation surface 108A from the solution medium due to the electric field generated from the array of electrodes 107. Generally, the large-scale non-uniform electric field is created at the furrow 104 between each electrode which can generate long range EK fluid flow and transport target entities in the bulk to the region close to the surface of the chip. The contoured operation surface 108A, particularly with the wells/recesses 101, modifies local electric field distribution and enhance short region EK performance.

The major effective EK activities include Dielectrophoresis (DEP), AC Electroosmosis (ACEO), and AC Electrothermosis (ACET). The overall phenomenon is always a combination of multiple effects. ACEO and ACET are categorized as electrohydrodynamic effects, which induces long range fluid flow in the solution medium. DEP is short-ranged motion on particles. As illustrated in FIG. 4, ACEO and ACET are responsible for generating fluid flow for long range transportation 110, and DEP takes part in short range confinement/short range fluid transport/localized regulation 111. With induced long range fluid flow 110, particle-like entities including charged or uncharged particles, sized from micron to submicron can be transported effectively close to the operation surface 108A. The wells/recesses 101 patterned on the operation surface 108A further regulates the local electric field and thus the target particles close to the operation surface 108A is concentrated by DEP forces inside the wells/recesses 101.

In more detail, ACEO arises due to the interaction between the electric double layer (EDL) formed at the interface between a solution and a charged solid surface like the operation surface 108A and an electric field in the tangential direction (i.e. $E_t$) to drive the ions in the diffuse layer of the EDL. When a pair of planar electrodes is charged with opposite polarity, the electric field is stronger at the gap and weaker at the electrode centre, therefore the $E_t$. The certain circumstances, there exist another electrohydrodynamic effect, known as ACET, which is due to the interaction between the electric field and the gradient of fluid properties. Since AC electric field can induce Joule heating in the solution medium and is more significant in the region of high field strength, the regional temperature change induces variation of fluid density, and thus conductivity and permittivity. For a planar electrode pair, ACET can form circulation from the electrode gap, and stir the bulk fluid in micro-scaled range. In summary, long range fluid flows can be generated using various classical electrode patterns, such as the parallel, castellated, quadrupole etc.

For short range manipulation, DEP effects become more promising as the field strength as well as its gradient are high. The structure that can induce sharp field gradient is the edges of wells/recesses 101 being patterned on the operation surface 108A. This localized force field enables designated driving patterns for short range collection 111 of the target entities.

Furthermore, it is possible to control patterns of fluid flow and particle collection by changing the applied voltage, frequency and formation of the AC electric field.

The mechanism can be used for enhancing biochemical reaction efficiency between target molecules suspended in the solution medium and counterpart molecules e.g. probe entities 109 immobilized on the operation surface 108A.

The contoured operation surface 108A above the electrode array 107 generates gradients of electric field and alters DEP, ACEO and ACET at specific. Depending on the frequency of the electric field and the conductivity of the solution medium, direction of the long range transportation 110 as well as that of the short range confinement/short range fluid transport/localized regulation 111 can be manipulated. Voltage is more related to the overall strength of EK effects, i.e. DEP force is proportional to $\nabla|E^2|$ in magnitude.

Figures 4A, 4B, 4C, 4D:
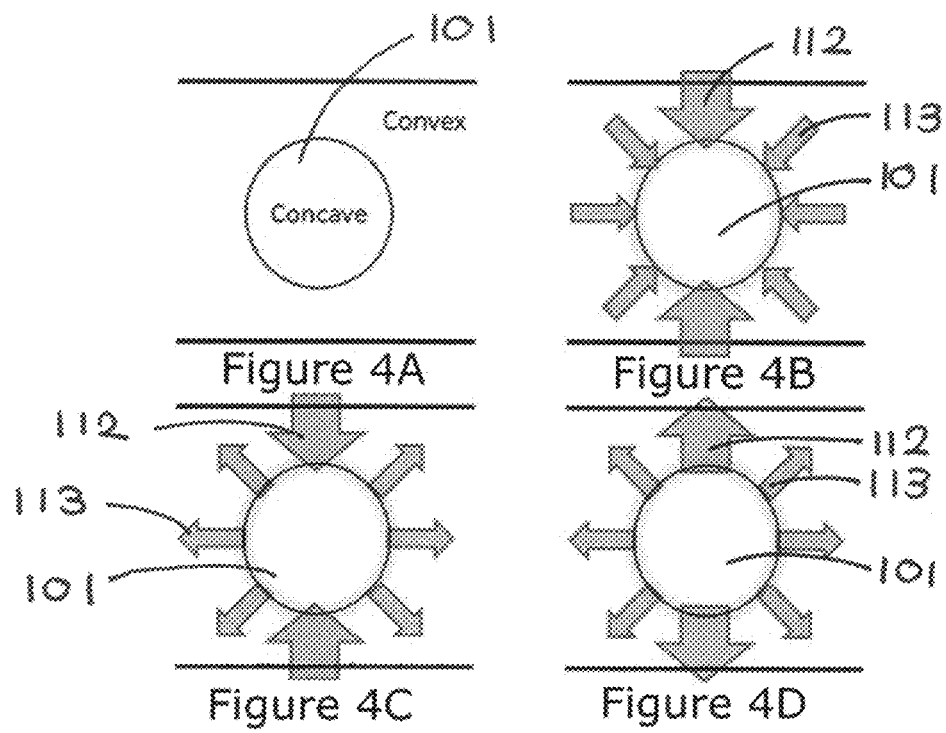
FIGS. 4A to 4D are schematic representations of a EK operation of a circular recess in the biochip of FIG. 1A. Specifically.

FIG. 4A to 4D is a schematic illustration of the direction of the long range EK flow 112 and the short range EK flow 113, hence the particle concentration inside and outside the well/recess 101 when different voltage, frequency and formation of the AC electric field is applied to the electrode array 107. The long and short range EK flow directly constitute the long range transportation 110 and short range confinement/short range fluid transport/localized regulation 111 respectively for transporting the target entities in the solution medium. In FIG. 4A, show a top plan view of the well/recess 101 on the contoured operation surface 108A. FIG. 4B shows the direction of the EK flows 112/113 when a low frequency electric field is applied. The main stream of EK flows 112/113 are pointing to the centre of the electrode, and the localized gradient at the edge of well/recess 101 directs particles towards the centre of the well/recess 101 and the electrode 107. FIG. 4C shows the direction of the EK flows 112/113 when a medium frequency electric field is applied. The main stream of EK flow 112 are pointing to the centre of the electrode 107, and the localized gradient 113 at the edge of well/recess 101 directs particles away from the centre of the well/recess 101 and the electrode 107. FIG. 4D shows the direction of the EK flow 112/113 when a high frequency electric field is applied. The main stream of EK flow 112 and the localized gradient 113 at the edge of well/recess 101 directs particles away from the centre of the well/recess 101 and the electrode 107. As adjacent wells/recesses 101 are separated by a furrow 104, when the main stream EK flow 112 and the localized gradient 113 are directed away from the centre of the well/recess 101, they are directed towards the furrow 104. The situation in FIG. 4B is most optimal when the probe entities 109 are attached inside the well/recess 101. The condition in FIGS. 4C and 4D is most optimal when the probe entities 109 are attached to the operation surface 108A outside the well/recess 101 or in the furrow 104.

With the contoured operation surface 108A, we are able to manipulate target entities collection pattern on the operation surface 108A using different frequencies, voltages and formations of the AC electric field. We are able to pattern the operation surface 108A in matrix or in any asymmetric arrangement on the electrodes 107, depending on specific applications.

Figure 9A:
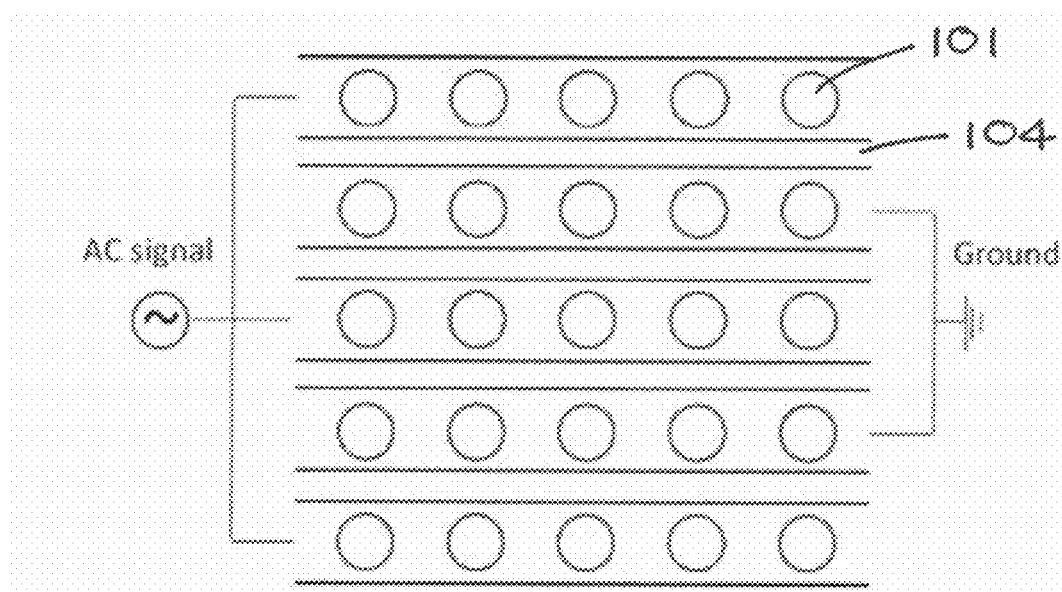
FIG. 9A is a schematic illustration of the electric connection of the biochip in FIG. 1A.

As shown in FIG. 9A there is an example of an operation surface with an N by N well/recess matrix array, where N is an odd number. The biochip 100 is fabricated on 8' wafers, and diced and assembled in PCBs with circuitry and adaptor connect to an external power supply. All odd electrode stripes 107 are connected to AC signal, and the rest even electrode stripes 107 are connected to the ground. AC electric field is supplied with an artificial function generator, Agilent 33250A. $SiO_2$ beads are used in this example (Sigma S5631) to illustrate the effect of frequency of the applied electric field to the active distribution of target entities. The beads are ranged from 0.5-10 um (80% between 1-5 um), and are suspended in DI $H_2O$ with conductivity of 5.5 uS/m. 30 ul of the beads solution is dispensed on the operation surface 108A, covering the microelectrode array and the EK manipulation process is recorded via Nikon eclipse i50 microscope under white light.

Figure 9B:
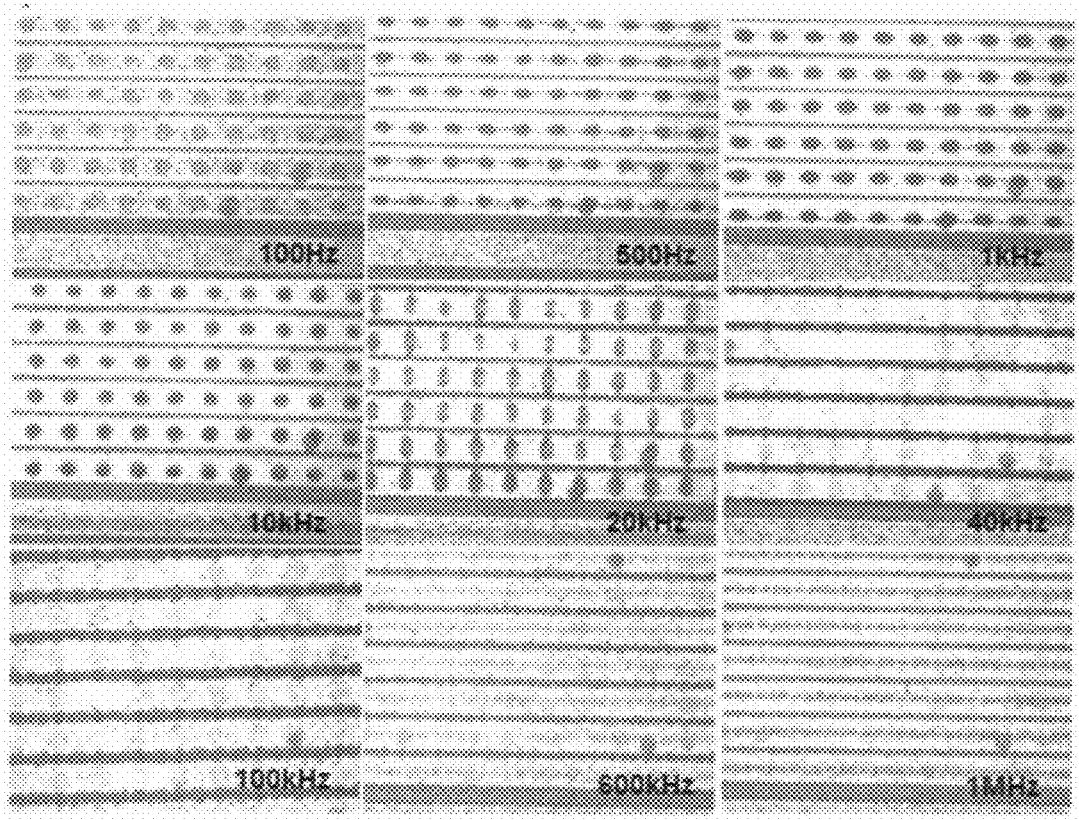
FIG. 9B is a photographical illustration of the biochip in FIG. 9A showing distribution of suspended target entities on the biochip at different frequencies of electric field applied across the electrodes.

The images in FIG. 9B were collected to demonstrate the transportation and focusing effect of using patterned N by N matrix operation surface 108A. The applied AC signal is 20 Vpeak-to-peak sinewave, with frequency varying from 100 Hz to 1 MHz.

When started at 100 Hz, beads started moving slowly. As frequency gradually increased to several kHz, the movement became more dramatic, and the centre of the well/recess 101 became more concentrated with beads. It was observed that, between 100 Hz to 500 Hz, the beads were drawn towards the centre of the electrode and the well/recess 101 and remained around the line of geometric symmetry. It was also observed that, as frequency increased above 500 Hz, the beads collected at the centre line started to be dragged into the nearest well/recess 101. Consequently, the "line" split into "dots". This was due to the profile described in FIG. 4B.

The most discrete round shape of beads cluster is observed when the frequency of the electric field is 10 kHz. As frequency increases beyond 10 kHz, the beads cluster started to deform and moves outside the well/recess 101 or the centre of the electrode 107 toward the edges of the electrode 107. It was then observed that the beads were circulating from the edge of the electrode 107 towards the electrode centre, arising, and falling back to the edge region. The width of circulation became narrower as frequency increased. This process of transition was dramatic around 10 kHz to 20 kHz, and at 40 kHz, most beads were drawn into the furrows 104 and the gap of the electrodes 107, as described in FIG. 4D.

From 40 kHz to 100 kHz, the width of circulation reaches minimum and the beads vibrate at electrode 107 edge, while some large sized beads exhibited self-rotation. Above 100 kHz, beads formed chains perpendicular to the electrode between the furrows 104. The chains were then broken at around 600 kHz, and beads were repelled to the centre of the electrodes 107 and furrows 104. This effect becomes more significant at 1 MHz. The reason why beads formed lines other than discrete dots as in low frequencies was because the dominating mechanisms of the fluid flow were different. More specifically, at low frequencies, beads experience ACEO induced fluid flow, which is sensitive to surface structures. The concave structure could regulate the flow and direct the beads inwards. While at high frequencies like in MHz level, ACEO no longer existed, ACET took dominance, which circulated beads from the bulk, and was less sensitive to surface structures.

Figure 10:
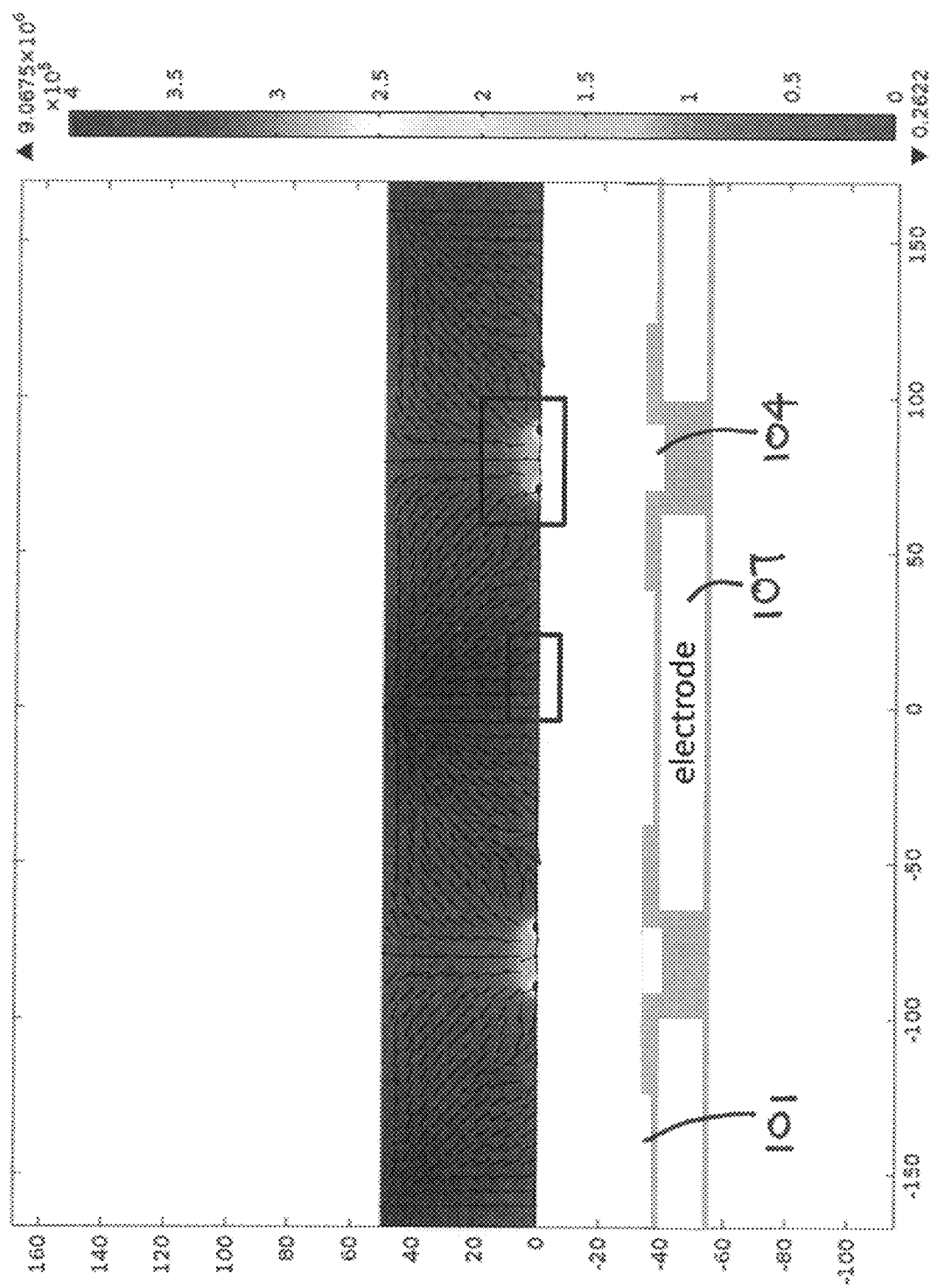
FIG. 10 is a schematic illustration of the electric field distribution and the direction of DEP force, shown by arrows, in a medium on the biochip under an AC electric field at a frequency of 1 kHz.

Referring to FIG. 10, there is shown the simulated DEP force field (red arrow) in a high conductivity solution medium with high frequency electric field. All arrows are directed away from the electrodes 107 and recesses 101.

Figure 11B:
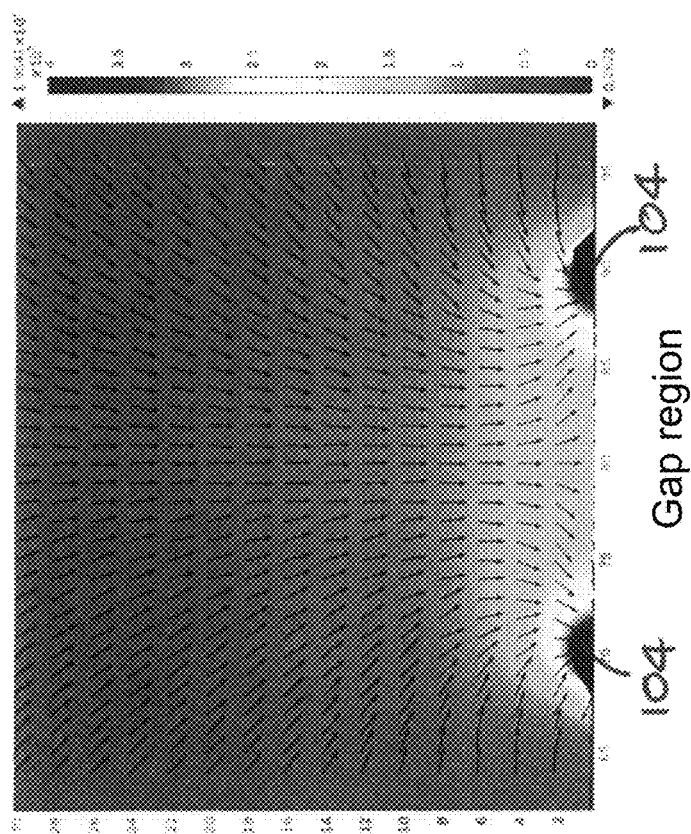
FIG. 11B is a schematic illustration of the electric field distribution and the direction of DEP force, shown by arrows, around a gap region between two recesses in the biochip of FIG. 11A in a low conductivity medium under an AC electric field of low frequency at 1 kHz.
Figure 11A:
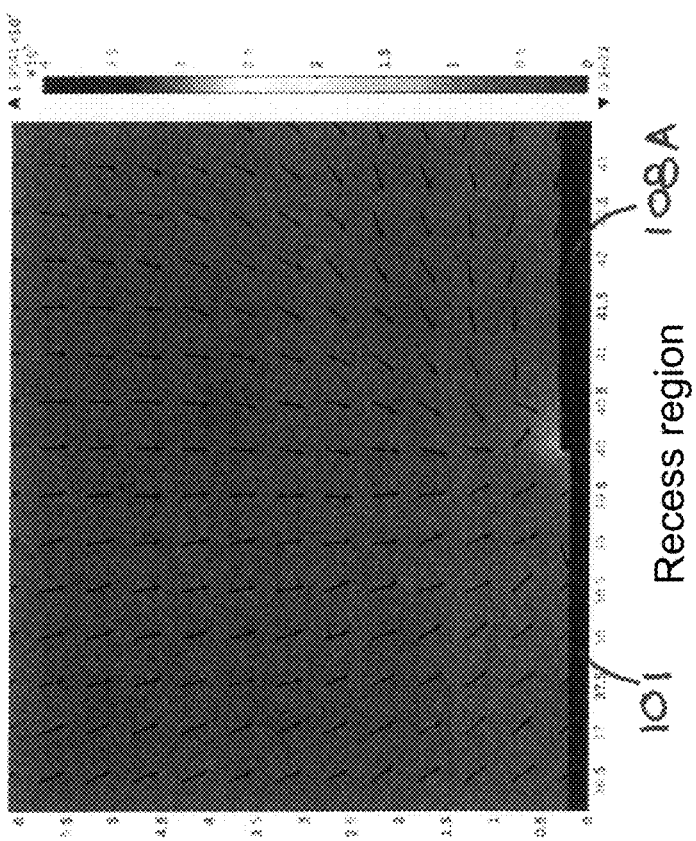
FIG. 11A is a schematic illustration of the electric field distribution and the direction of DEP force, shown by arrows, around the recess in the biochip in a low conductivity medium under an AC electric field of low frequency at 1 kHz.
Figure 12B:
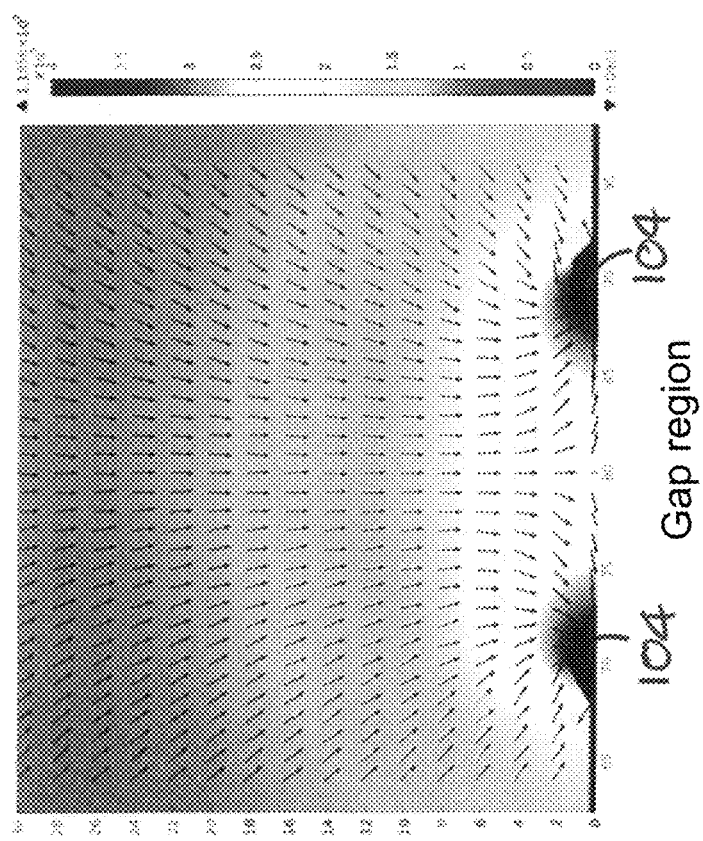
FIG. 12B is a schematic illustration of the electric field distribution and the direction of DEP force, shown by arrows, around a gap region between two recesses in the biochip of FIG. 12A in a low conductivity medium under an AC electric field of medium frequency at 10 kHz.
Figure 12A:
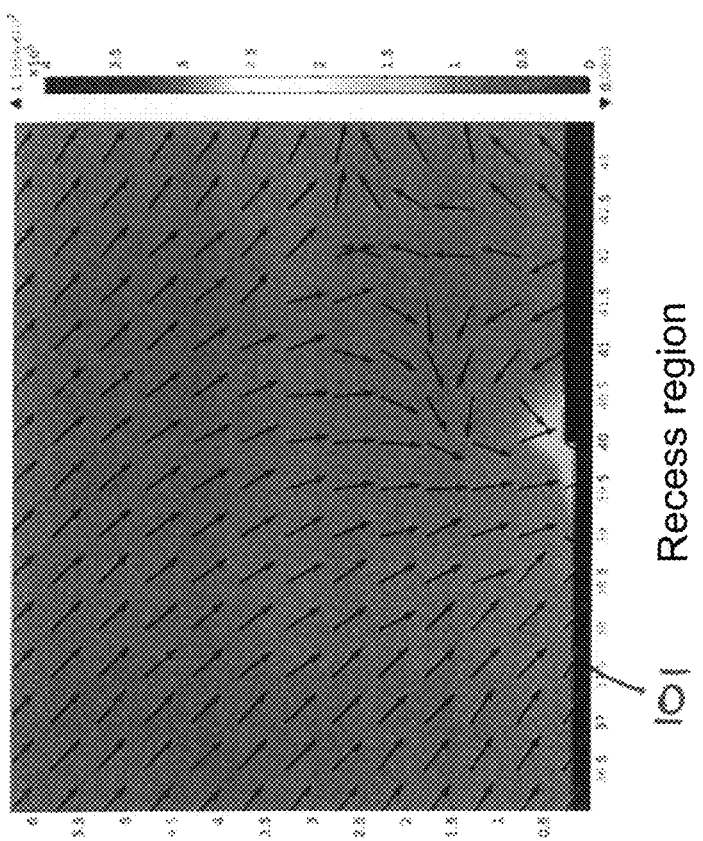
FIG. 12A is a schematic illustration of the electric field distribution and the direction of DEP force, shown by arrows, around the recess in the biochip in a low conductivity medium under an AC electric field of medium frequency at 10 kHz.
Figure 13B:
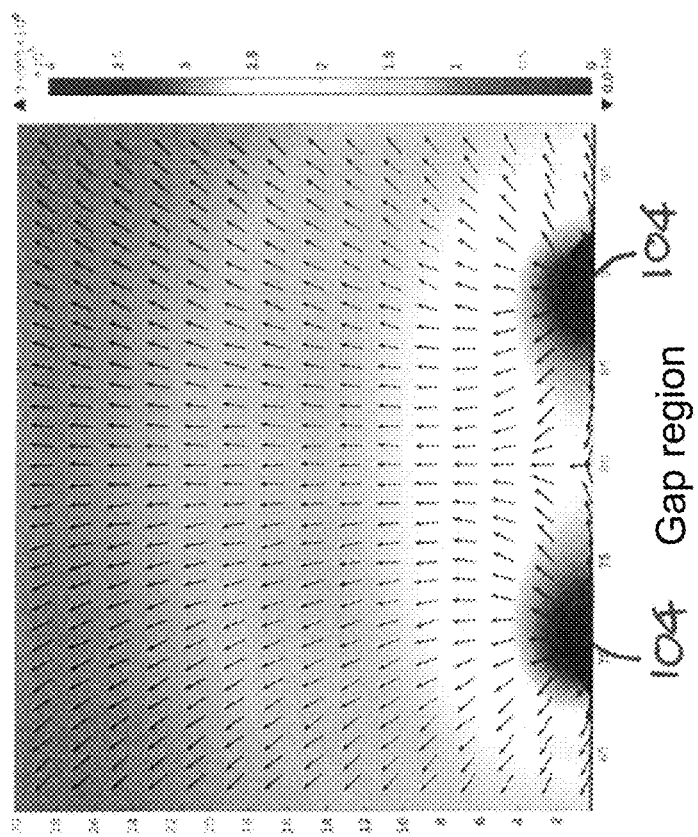
FIG. 13B is a schematic illustration of the electric field distribution and the direction of DEP force, shown by arrows, around a gap region between two recesses in the biochip of FIG. 13A in a low conductivity medium under an AC electric field of high frequency of 1 MHz.
Figure 13A:
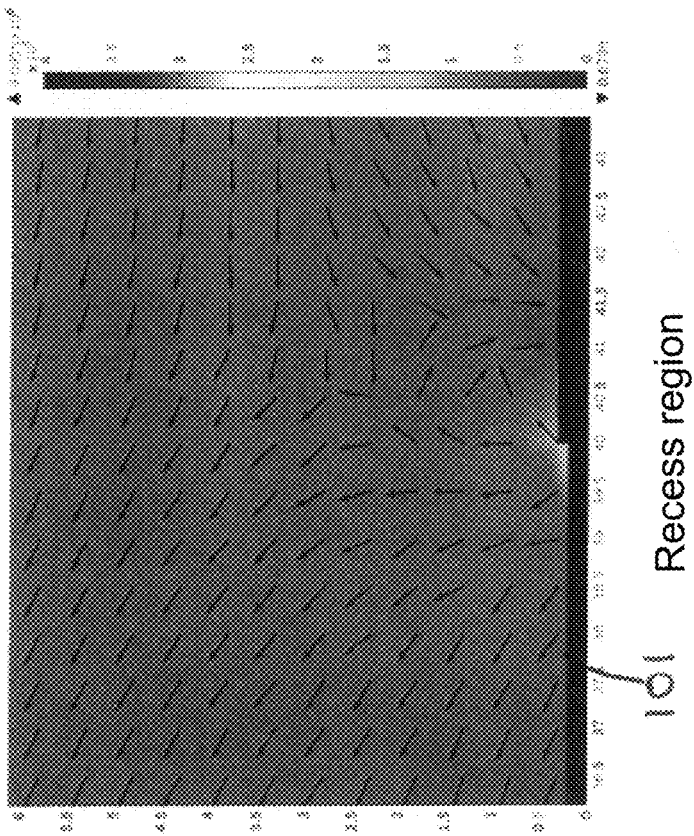
FIG. 13A is a schematic illustration of the electric field distribution and the direction of DEP force, shown by arrows, around the recess in the biochip in a low conductivity medium under an AC electric field of high frequency of 1 MHz.
Figure 14B:
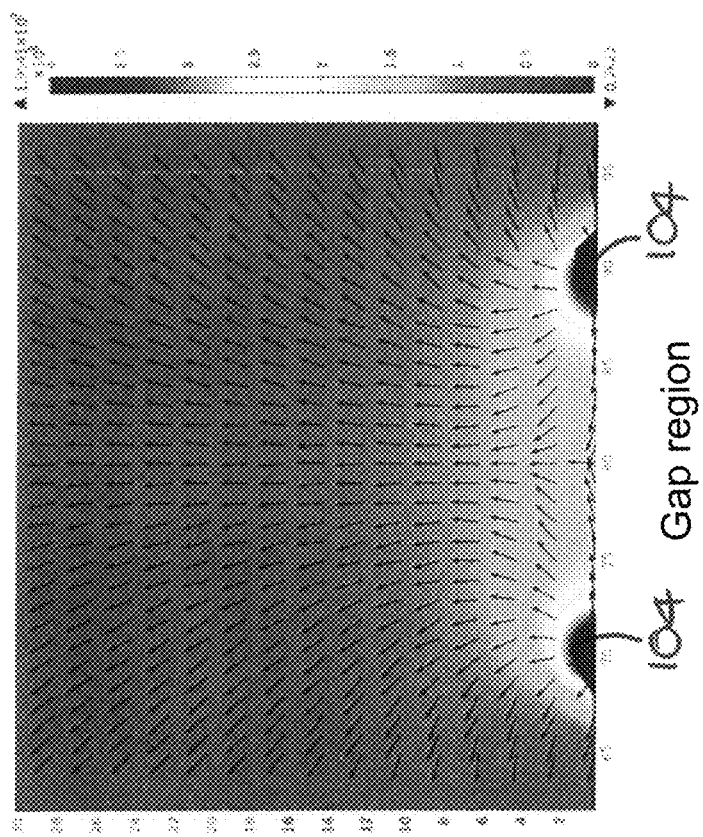
FIG. 14B is a schematic illustration of the electric field distribution and the direction of DEP force, shown by arrows, around a gap region between two recesses in the biochip of FIG. 14A in a high conductivity medium under an AC electric field of low frequency of 1 kHz.
Figure 14A:
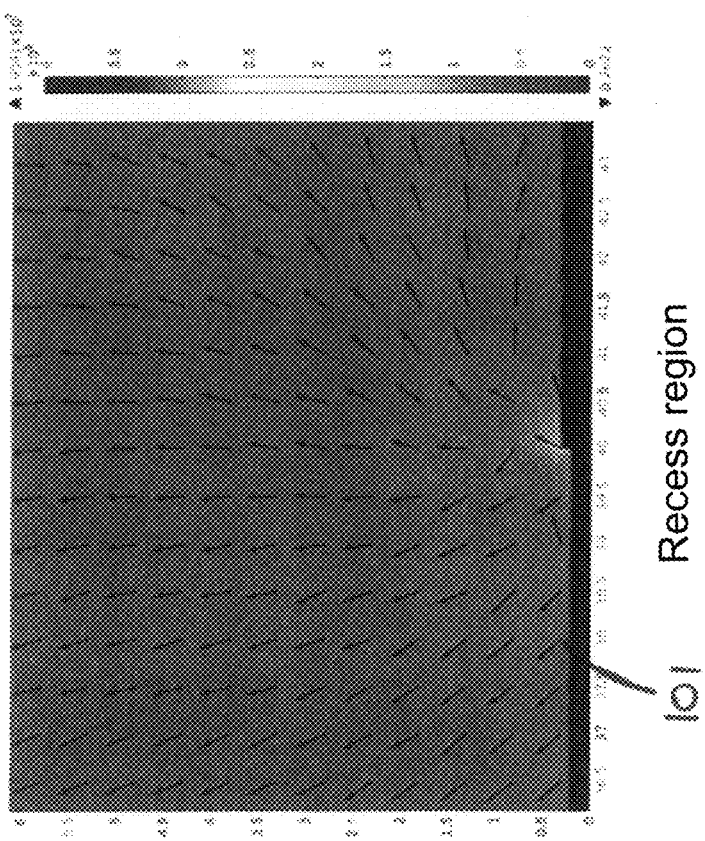
FIG. 14A is a schematic illustration of the electric field distribution and the direction of DEP force, shown by arrows, around the recess in the biochip in a high conductivity medium under an AC electric field of low frequency of 1 kHz.
Figure 15B:
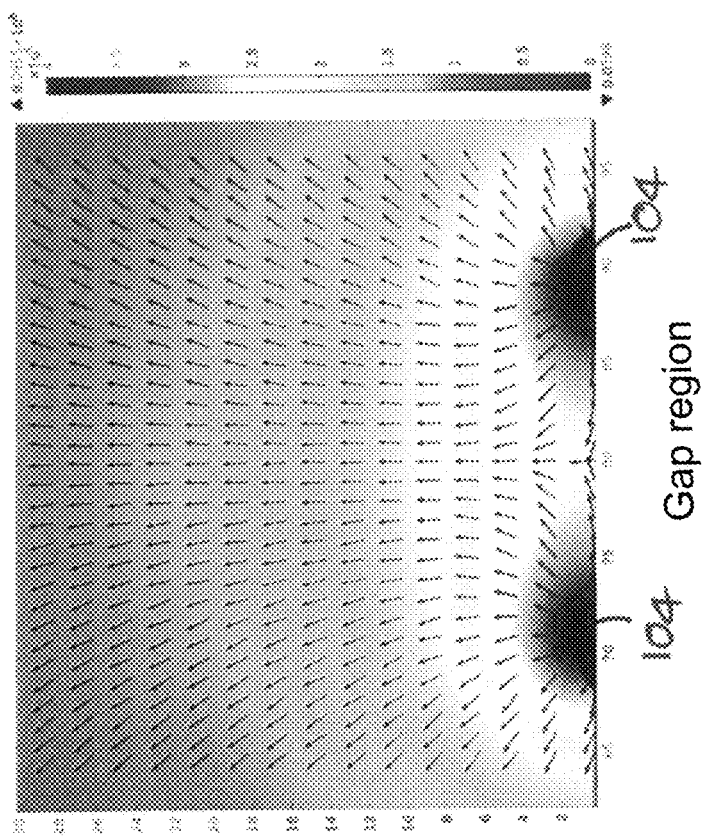
FIG. 15B is a schematic illustration of the electric field distribution and the direction of DEP force, shown by arrows, at an area around a gap region between two recesses in the biochip of FIG. 15A in a high conductivity medium under an AC electric field of high frequency of 1 MHz.
Figure 15A:
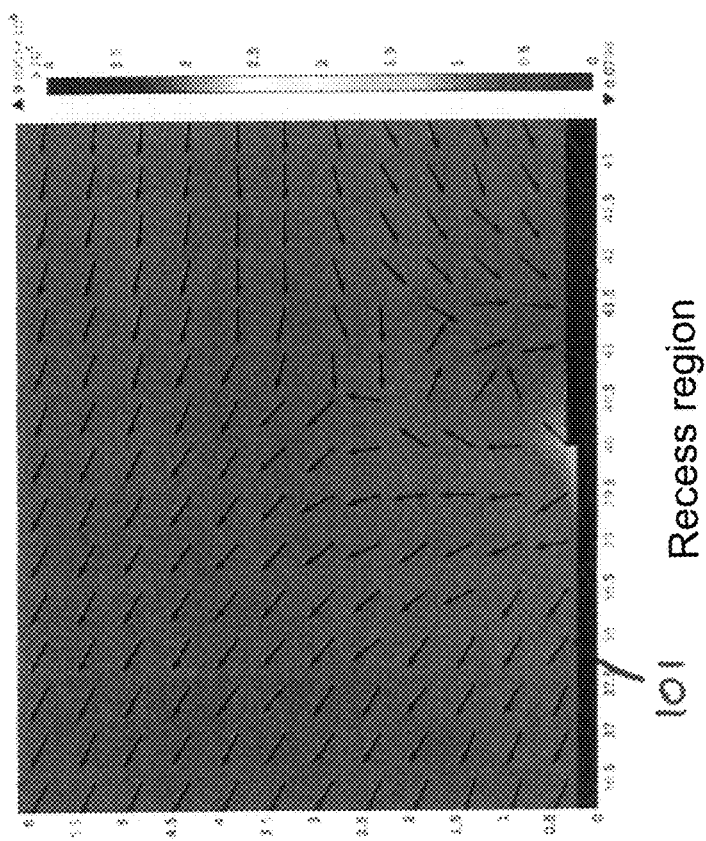
FIG. 15A is a schematic illustration of the electric field distribution and the direction of DEP force, shown by arrows, around the recess in the biochip in a high conductivity medium under an AC electric field of high frequency of 1 MHz.

Turning to FIGS. 11A and 11B, in a low conductivity medium and with low frequency electric field, the DEP force, shown by arrows, is directed towards the well/recess 101 and the furrow 104 and away from the operation surface 108A adjacent the well/recess 101. The same applies when the solution medium is of low conductivity and a medium frequency electric field is applied (see FIGS. 12A and 12B) except that the local field is more concentrated towards the well/recess 101. In a low conductivity medium and high frequency electric field as shown in FIGS. 13A and 13B, the DEP force is directed away from the well/recess 101 and the furrow 104 but towards the operation surface 108A adjacent the well/recess 101. In FIGS. 14A and 14B, when the conductivity of the medium is high and the frequency of the electric field is low, the DEP force directs away from the well/recess 101 and the furrow 104 but towards the operation surface 108A adjacent the well/recess 101. In FIGS. 15A and 15B, when the solution medium is of high conductivity and the electric field is at high frequency, the DEP force are directed away from the well/recess 101 and the furrow 104 but towards the operation surface 108A adjacent the well/recess 101.

In summary of a specific biochip design described above, in a high conductivity medium, even if the applied electric field has a low frequency, the DEP force is directed away from the well/recess 101. To direct the DEP force towards the well/recess 101, low conductivity medium should almost always be used. When directing the DEP force away from the well/recess 101, a high frequency should be used and the conductivity of the medium is not of a major concern. This may not be a universal solution that only low to medium frequencies and low conductive medium can direct entities into the array of well/recess 103. The design of electrode 107 and the well/recess 103 pattern are more crucial for modulating combinations of EK forces and therefore the target entities in or out of the well/recess 103. The design of the electrode 107 and the well/recess 103 structures may include the material, scales or shapes thereof.

Figure 2:
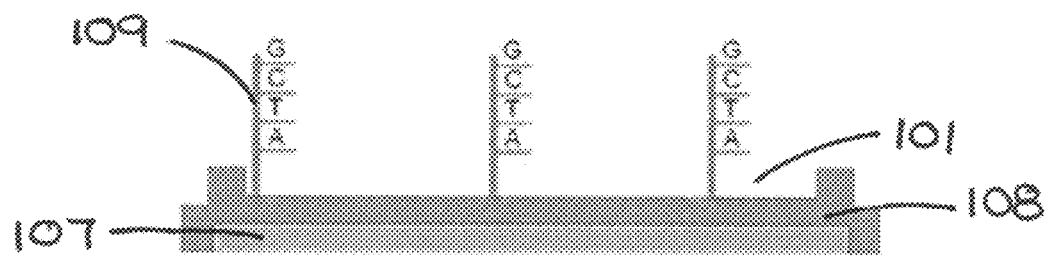
FIG. 2 is a schematic side view of part of the biochip in FIG. 1A showing a recess with probe entities attached thereto on an operation surface and an electrode.
Figure 3:
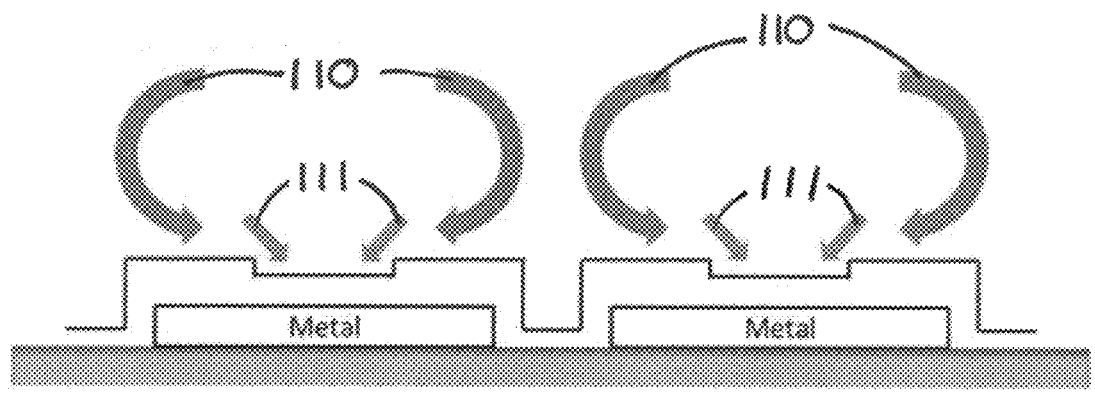
FIG. 3 is a schematic representation of a part of the biochip in FIG. 1A with indications showing a long range fluid transport and a short range fluid transport or localized regulation.
Figure 5:
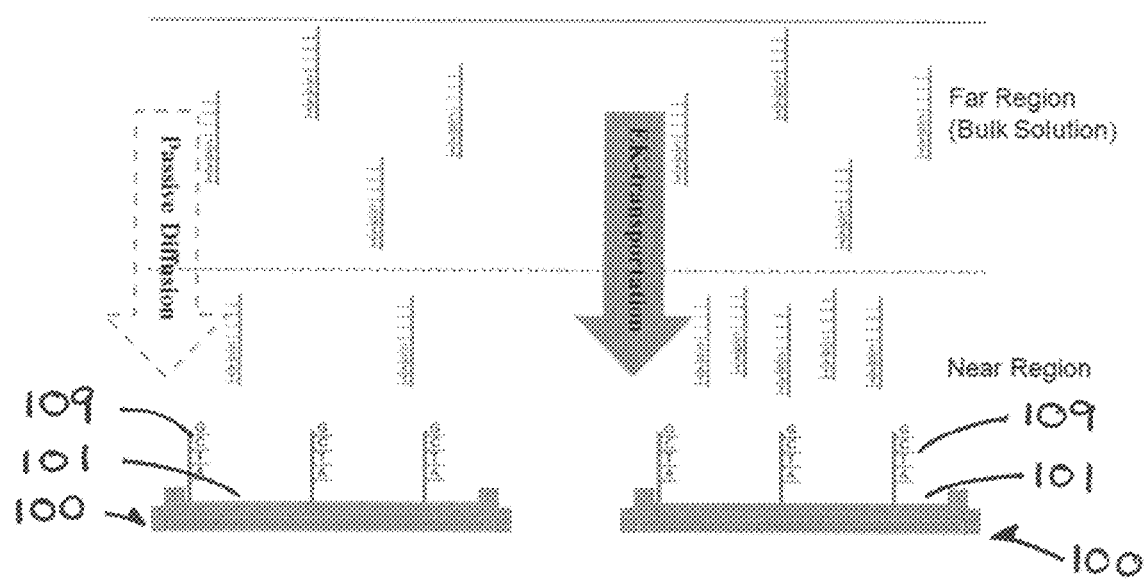
FIG. 5 is a schematic illustrative comparison between binding of target and probe entities via passive diffusion and that via electrokinetically enhanced transportation.

The biochip 100 produces even better results by enhancing the EK assisted hybridization. As shown in FIG. 2, probe entities are attached via surface engineering to the operation surface 108A by covalent bonds to a chemical matrix in a conventional manner. The aim of the biochip 100 according to the invention is to enhance interaction between the target entities in the solution medium and probe entities 109 on the operation surface 108A by using Electrokinetic (EK) effects. A simulated comparison between passive hybridization and EK assisted hybridization is shown in FIG. 5. FIG. 16 is a photographic comparison between two biochips, the left shows the result of EK assisted hybridization and the right shows the results of passive hybridization. Clearly EK assisted hybridization produces better results. FIG. 18 is the artificial unit intensity representation of the hybridization result on the two biochips in FIG. 16.

Figure 6:
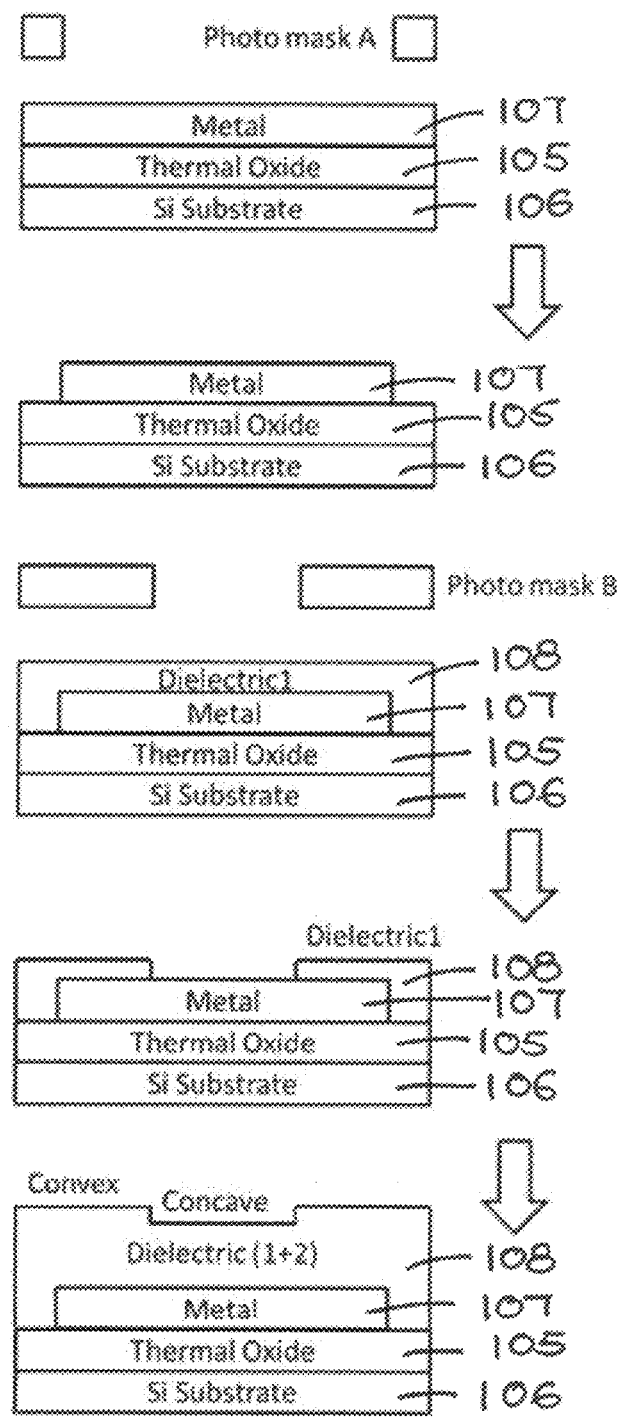
FIG. 6 is a schematic illustration of a first embodiment of a fabrication process of the biochip in FIG. 1A.

We now turn to the fabrication method of the biochip 100. The preferred method is shown in FIG. 6.

The process is based on a CMOS compatible microelectronic fabrication. On a silicon substrate 106, a thickness of oxide layer 105 is produced by thermal oxidation, and a metal layer 107 is constructed via aluminum sputtering. The electrode arrays are formed by dry etch of the metal layer 107. Following metallization process, silicon oxide ($SiO_2$) dielectric layer 108 is deposited via PECVD over the upper surface defined by the metal layer 107. The array of wells/recesses 101 as well as the wire-bonding pad micro-indentations are patterned and opened by dry etching. Then, a second $SiO_2$ layer 108 with thickness is deposited over the first $SiO_2$ layer using PECVD. The chip fabrication completes with a final dry etch process for complete opening of the wire-bonding pads. Further process involves surface treatment of the biochip 100 for immobilization of probe entities 109 into each well/recess 101. The biochip 100 is now ready for use.

Figure 7:
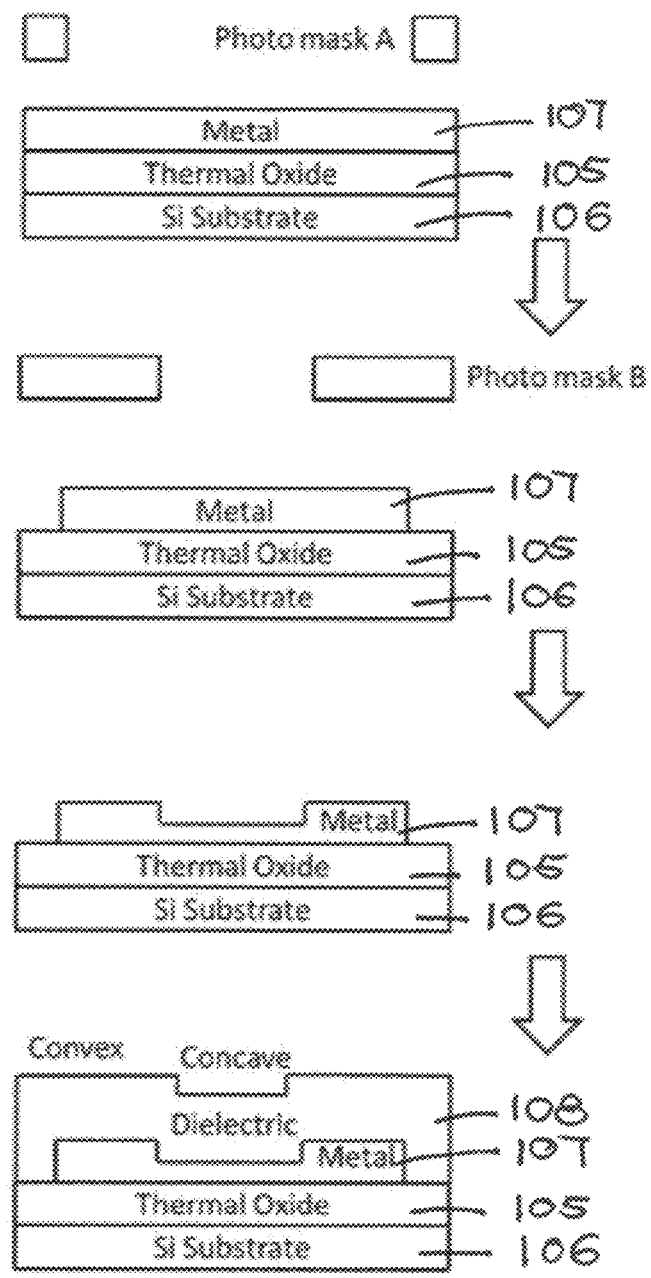
FIG. 7 is a schematic illustration of a second embodiment of the fabrication process of the biochip in FIG. 1A.

Referring to FIG. 7 showing a process based on a CMOS compatible microelectronic fabrication. On a silicon substrate 106, a thickness of oxide layer 105 is produced by thermal oxidation, and a metal layer 107 is constructed via aluminum sputtering. The electrode arrays 107 are formed by dry etching of this metal layer 107. Another mask is applied for the well/recess 101 patterning, and etching follows, to create the well/recess 101 on metal electrodes 107. After that, a silicon oxide ($SiO_2$) dielectric layer is deposited via PECVD over the upper surface of the metal layer 107. The wire-bonding pad micro-indentations are patterned and opened by dry etching.

Figure 8:
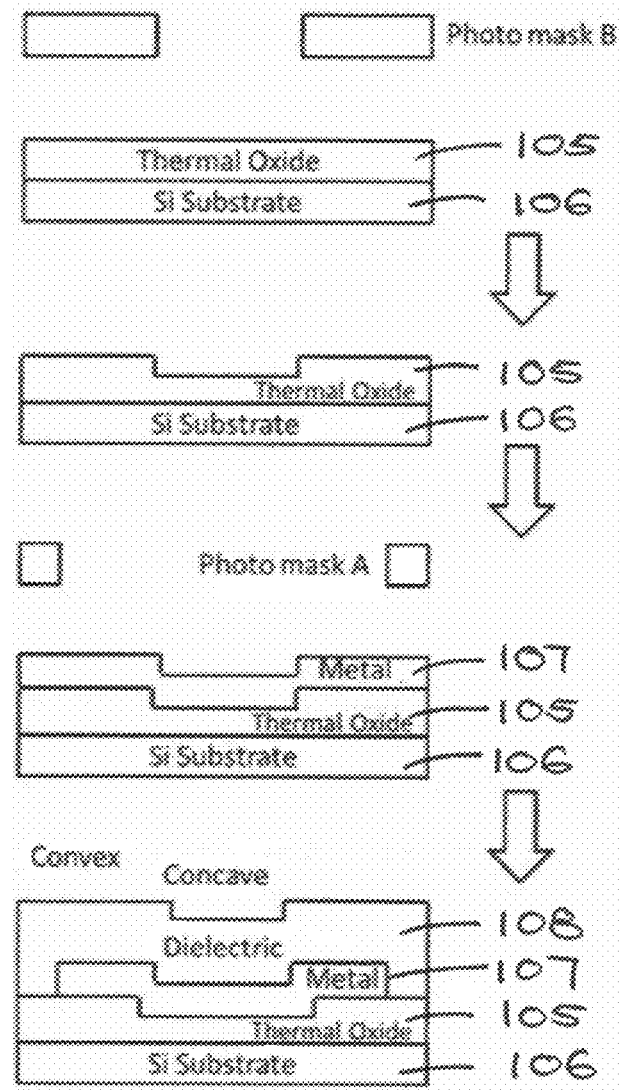
FIG. 8 is a schematic illustration of a third embodiment of the fabrication process of the biochip in FIG. 1A.

Referring to FIG. 8 which is again based on a CMOS compatible microelectronic fabrication. On a silicon substrate 106, a thickness of oxide layer 105 is produced by thermal oxidation. We apply photo mask for patterning wells/recesses 101, and perform dry etching on the thermal oxide layer 105. After that the wells/recesses 101 are formed on the oxide layer 105. A metal layer of is deposited on the upper surface of the oxide layer 105 and constructed via aluminum sputtering. The electrode arrays are formed by dry etching of this metal layer 107. After that, a silicon oxide ($SiO_2$) dielectric layer is deposited via PECVD over the upper surface defined on the metal layer 107. The wire-bonding pad micro-indentations are patterned and opened by dry etching.

The invention has been given by way of example only, and various other modifications of and/or alterations to the described embodiment may be made by persons skilled in the art without departing from the scope of the invention as specified in the appended claims.

The invention claimed is:

1. A method of fabricating a biochip, comprising:
   a) providing a base member;
   b) photomasking an upper surface on the base member;
   c) etching two or more recesses on the upper surface;
   d) depositing a dielectric material on an upper layer over the two or more recesses;
   wherein the two or more recesses define a contour on the upper surface, the dielectric material adopts the contour and hardens to form a contoured operation surface, and wherein a second round of steps b) and c) are conducted on the upper surface and between the two or more recesses to create a further recess therebetween which defines the upper layer on which step d) is performed.

2. A method of fabricating a biochip, comprising:
   a) providing a base member;
   b) photomasking an upper surface on the base member;
   c) etching two or more recesses on the upper surface;
   d) depositing a dielectric material on an upper layer over the two or more recesses;
   wherein the two or more recesses define a contour on the upper surface, the dielectric material adopts the contour and hardens to form a contoured operation surface, and wherein the base member includes at least a thermal oxide layer which defines the upper surface and a first round of steps b) and c) are conducted on the upper surface to define the contour.

3. The method as claimed in claim 2, further comprising depositing a layer of metal onto the upper surface to form a further upper surface which adopts the contour.

4. The method as claimed in claim 3, wherein a second round of steps b) and c) is conducted on the further upper surface to create a further recess between the two or more recesses to further define the contour and form the upper layer.

5. The method as claimed in claim 4, wherein a step d) is conducted on the upper layer such that the dielectric material adopts the further defined contour and hardens to form a contoured operation surface.

6. A method of fabricating a biochip, comprising:
   a) providing a base member which includes a metal layer deposited on a thermal oxide layer;
   b) photomasking an upper surface on the metal layer;
   c) etching two or more recesses on the upper surface;
   d) depositing a dielectric material on the upper surface forming an upper layer over the two or more recesses;
   e) photomasking the upper layer;
   f) etching a recess on the upper layer;
   g) depositing a dielectric material on the upper layer over the recesses;
   wherein the recesses define a contour on the upper surface and the upper layer, the dielectric material adopts the contour and hardens to form a contoured operation surface.

7. A method of fabricating a biochip, comprising:
   a) providing a base member which includes a metal layer deposited on a thermal oxide layer, the metal layer defines the upper surface on which a first round of steps b) and c) are conducted to form the two or more recesses;
   b) photomasking an upper surface on the base member;
   c) etching two or more recesses on the upper surface;

d) conducting a second round of steps b) and c) on the upper surface and between the two or more recesses to create a further recess therebetween which defines an upper layer;
e) depositing a dielectric material on an upper layer over the recesses;
wherein the recesses define a contour on the upper layer, the dielectric material adopts the contour and hardens to form a contoured operation surface.

8. A method of fabricating a biochip, comprising:
a) providing a base member which includes at least a thermal oxide layer which defines the upper surface and a first round of steps b) and c) are conducted on the upper surface;
b) photomasking an upper surface on the base member;
c) etching a recess on the upper surface;
d) depositing a layer of metal onto the upper surface to form a further upper surface which adopts the contour of the upper surface;
e) a second round of steps b) and c) is conducted on the further upper surface to create further recess on either side of the first formed recess to further define the contour and form the upper layer
d) depositing a dielectric material on an upper layer over the recesses;
wherein the dielectric material adopts the contour on the upper layer and hardens to form a contoured operation surface.

* * * * *